United States Patent [19]
Camaioni et al.

[11] Patent Number: 5,585,515
[45] Date of Patent: Dec. 17, 1996

[54] METHOD AND REACTION PATHWAY FOR SELECTIVELY OXIDIZING HYDROCARBON COMPOUNDS

[75] Inventors: Donald M. Camaioni; Michael A. Lilga, both of Richland, Wash.

[73] Assignee: Battelle Memorial Institute, Richland, Wash.

[21] Appl. No.: 56,577

[22] Filed: Apr. 30, 1993

Related U.S. Application Data

[63] Continuation of Ser. No. 679,689, Apr. 3, 1991, abandoned.

[51] Int. Cl.$^6$ .......................... C07C 69/63; C07C 27/10; C07C 27/12; C07C 27/16
[52] U.S. Cl. ............................................ 560/227; 568/910
[58] Field of Search ............................. 560/227; 568/910

[56] References Cited

U.S. PATENT DOCUMENTS

| | | | |
|---|---|---|---|
| 3,917,708 | 11/1975 | Kuessner et al. | 260/586 R |
| 4,199,533 | 4/1980 | Benson | 585/500 |
| 4,321,207 | 3/1982 | Cesark | 260/674 |
| 4,444,984 | 4/1984 | Jones et al. | 585/500 |
| 4,517,374 | 5/1985 | Sanderson et al. | 549/533 |
| 5,233,113 | 8/1993 | Periana et al. | 585/500 |
| 5,306,855 | 4/1994 | Periana et al. | 585/500 |

OTHER PUBLICATIONS

Gretz et al. *Journal of the American Chemical Society*, 109, 8109–8111 (1987).
"Novel Approach Taken For Methane Activation" Technology, Jan. 19, 1988, C&EN, p. 27.
Gretz et al., "Carbon–Hydrogen Bond Activation by Electrophilic Transition–Metal Compounds. Palladium (II)-Mediated Oxidation Of Arenes and Alkanes Including Methane" J. Am. Chem. Soc. 1987, 109, 8109–8111.
Kinoshita, et al., "Aerial Oxidation of Benzene in the Presence of Electrochemically Generated Cuprous Ions", Angew. Chem. Suppl., 1983, 599–608.
Kunai et al., "The Role of Oxygen in the Hydroxylation Reaction of Benzene with Fenton's Reagent 18O Tracer Study", J. Am. Chem. Soc. 1986, 108, pp. 6012–6016.
Kunai, et al., "Mechanistic Study of Air Oxidation of Benzene in Sulfuric Acid Catalyzed by Cuprous Ions", J. Org. Chem. 1986, 51, pp. 3471–3474.
Walling, "Fenton's Reagent Revisited", Accounts of Chemical Research, vol. 8, 1975, pp. 125–131.
Kirk–Othmer Encylcopedica of Chemical Terminology, Third Edition, vol. 12, 1980, pp. 826–851.
Leon M. Dorfman et al., "Reactivity of the Hydroxyl Radical in Aqueous Solutions", U.S. Dept. of Commerce, National Bureau of Standards, 1973, pp. 1–62.
G. E. Keller et al., "Synthesis of Ethylene via Oxidative Coupling of Methane", Journal of Catalysis, 73, 1982, pp. 9–19.
Dubasi Rao et al., "Liquid of Cyclohexane to Adipic Acid in a Single Stage", Ind. Eng. Chem. Process Des. Dev., 1986, 25, pp. 299–304.

Mark S. Baker, et al., "The Effect of pH on Yields of Hydroxyl Radicals Produced From Superoxide by Potential Biological Iron Chelators", Archives of Biochemistry and Biophysics, vol. 246, No. 2, May 1, pp. 581–588, 1986.
F. Garcia–Ocho, et al., "A Comparison of Kinetic Data Interpretation Methods: Thermal Oxidation of n–Octane in Liquid Phase", The Chemical Engineering Journal, 39, 1988, pp. 47–54.
J. Haggin, "Union Carbide Pursuing Direct Conversion of Methane to Ethylene", C&EN News, vol. 66, No. 27, July 4, 1988, pp. 22–24.
Brooks et al., "A low–cost way to break into ethylene", Chemical Week, Jul. 24, 1985, 36–39.
C. L. Jenkins, et al., "Solvolytic Routes via Alkylcopper Intermediates in the Electron–Transfer Oxidation of Alkyl Radicals", J. Am. Chem. Soc., 94:3, Feb. 9, 1972, pp. 843–855.
Walling et al., "Role of Silver (II) in Silver–Catalyzed Oxidations by Peroxydisulfate$^1$", J. Org. Chem., vol. 43, No. 17, 1978, pp. 3266–3271.
Tien–Yau Luh et al., "Thermolysis of tert–Butyl Cubanepercarboxylate. The Cubyl Radical", J. Org. Chem., vol. 43, No. 17, 1978 pp. 3271–.
Kirk–Othmer Encylcopedia of Chemical Technology, Third Edition, vol. 1, 1978, pp. 510–531.

(List continued on next page.)

*Primary Examiner*—Gary Geist
*Assistant Examiner*—Barbara S. Frazier
*Attorney, Agent, or Firm*—Wells, St. John, Roberts, Gregory & Matkin P.S.

[57] ABSTRACT

A method of selectively oxidizing an organic compound in a single vessel comprises: a) combining an organic compound, an acid solution in which the organic compound is soluble, a compound containing two oxygen atoms bonded to one another, and a metal ion reducing agent capable of reducing one of such oxygen atoms, and thereby forming a mixture; b) reducing the compound containing the two oxygen atoms by reducing one of such oxygen atoms with the metal ion reducing agent to, 1) oxidize the metal ion reducing agent to a higher valence state, and 2) produce an oxygen containing intermediate capable of oxidizing the organic compound; c) reacting the oxygen containing intermediate with the organic compound to oxidize the organic compound into an oxidized organic intermediate, the oxidized organic intermediate having an oxidized carbon atom; d) reacting the oxidized organic intermediate with the acid counter ion and higher valence state metal ion to bond the acid counter ion to the oxidized carbon atom and thereby produce a quantity of an ester incorporating the organic intermediate and acid counter ion; and e) reacting the oxidized organic intermediate with the higher valence state metal ion and water to produce a quantity of alcohol which is less than the quantity of ester, the acid counter ion incorporated in the ester rendering the carbon atom bonded to the counter ion less reactive with the oxygen containing intermediate in the mixture than is the alcohol with the oxygen containing intermediate.

66 Claims, 3 Drawing Sheets

OTHER PUBLICATIONS

R. G. Minet et al., "Development of the Benson Process for Ethylene and Acetylene from Methane", Chemical Economy & Eng. Review, Oct. 1983, vol. 5, No. 10 (No. 172) pp. 35–37.

G. D. Menghani et al., "Kinetics of Oxidation of Ethanediol by Peroxydisulphate Catalysed by Silver Ions", Dept. of Chem., University of Jodhpur Paper. 1983.

Ahmed Khayar et al., "Calculation of Means Collision Cross Sections of Free Radical OH With Foreign Gases", J. Quant. Spctrosc. Radiat. Transfer, vol. 28, No. 3, 1982, pp. 199–212 (Great Britain).

E. I. Troyanskii, et al., "Regiospecific Oxidation of Alkanesulfonamides To 3-Oxoalkanesulfonamide", 1989 Plenum Publishing Corporation, pp. 1401–1405.

S. P. Prokopchuk et al., "Selection of Optimal Process Conditions For Production of Carboxylic Acids By Liquid–Phase Oxidation Of A Pentane Fraction", Khimicheskaya Promyshlennost, vol. 19, No. 7, pp. 15–17, 1987.

E. I. Troyanskii, et al., "Oxidation of Aliphatice Thioamides In A Sodium Peroxydsulfate–Cupric Chloride System", 1986 Plenum Publishing Corporation, pp. 1036–1041.

Robert McCelland, "Rate–Limiting Deprotonation in Thtrahedral Intermediate Breakdown", J. Am. Chem. Soc., 1984, 106, pp. 7579–7583.

Donald M. Camaioni, et al., "Carbon–Hydrogen vs. Carbon–Carbon Bond Cleavage of 1,2–Diarylethane Radical Cations In Acetronitrile–Water", *The Journal of Organic Chemistry, vol. 49, No. 9, pp. 1607–1613 (1984)*.

Deardurff, Larrie A., et al., "Products and Mechanism of the Oxidation of 9–Methylanthracene by Peroxydisulfate Proton Loss, etc.", *The Journal of Organic Chemistry*, vol. 51, No. 19, 3686–3693 (1986).

Steckhan, Eberhard, "Indirect Electroorganic Syntheses—A Modern Chapter of Organic Electrochemistry", *Angew. Chem. Int. Ed. Engl.*, vol. 25, pp. 683–701 (1986).

METHOD AND REACTION PATHWAY FOR SELECTIVELY OXIDIZING HYDROCARBON COMPOUNDS

Related Patent Application Data

This patent resulted from a continuation application of U.S. patent application Ser. No. 07/679,689 to Camaioni et al., entitled "Method and Reaction Pathway for Selectively Oxidizing Organic Compounds", which was filed on Apr. 3, 1991. The Ser. No. 07/679,689, application was abandoned in favor of the continuation application from which this patent matured.

TECHNICAL FIELD

This invention relates generally to selective oxidation of organic compounds.

BACKGROUND OF THE INVENTION

A need exists for a process that will enable selective oxidation of organic compounds to alcohols and olefins. However, stopping the oxidation of organic compounds at alcohols and olefins is difficult. For example, the ease of oxidation of carbon-hydrogen bonds increases in the order of, HC<H—C—OH<H—C=O<H—C(=O)OH. For this reason, oxidation reactions often give a complex array of extensively oxidized ketone and carboxylic acid products. Under some conditions, the oxidation reaction proceeds all the way to $CO_2$.

One long desired goal has been to provide an economical and controllable oxidation process whereby methane is converted into desired higher organic chemicals. This is due, in part, to the large and stable raw material supply of natural gas, with reserves estimated to be about 2180 trillion cubic feet in 1986. Few technologies have emerged, however, which are viable for direct methane conversion. An example of such technologies includes partial flame oxidation, electric-arc processes, oxidative couplings, and the Benson process. These methods typically involve very high temperatures or very aggressive reactants which provide poor selectivity and less than desirable efficiency. The prominent barrier to methane conversion is the strong C—H bond strength of 104 kcal/mol. The methane molecule is largely inert or, once enough energy is applied to cleave a C—H bond, continuing reactions are rapid and nonselective, with combustion being a prime example. The challenge in methane utilization is to carry out functionalization in a controlled, selective fashion so that valuable intermediate products, such as methanol, can be obtained.

Methane is not the only organic compound feed stock of which selective oxidation would be desired. For example, the oxidation of cyclohexane to a mixture of cyclohexanol and cyclohexanone is an important industrial process. The resultant ketone/alcohol mixture is used in the production of adipic acid, an important reagent in the synthesis of nylon 66. In the United States, 98% of the adipic acid produced is made by ketone/alcohol mixture oxidation and 90% of the acid is used for nylon manufacture. Ketone/alcohol mixture is also used in the production of ε-caprolactam, used in the manufacture of nylon 6. It would be desirable to develop a process for oxidation of cyclohexane which is substantially selective to cyclohexanol.

The conventional process of cyclohexane oxidation utilizes a cobalt catalyst and air as an oxidant. Typical conditions are 150°–160° C. and 8–10 atmospheres. To minimize over-oxidation, conversion per pass is limited to 4–6 mol percent. This requires that cyclohexane be distilled from the product mixture before recycling. Selectivity to the ketone/alcohol mixture is about 75–80%.

It is a principal objective of this invention to develop a process which is capable of oxidizing a wide range of organic compounds controllably to selected end products.

BRIEF DESCRIPTION OF THE DRAWINGS

Preferred embodiments of the invention are described below with reference to the accompanying drawings, which are briefly described below.

DETAILED DESCRIPTION OF THE PREFERRED EMBODIMENTS

Figure 1:
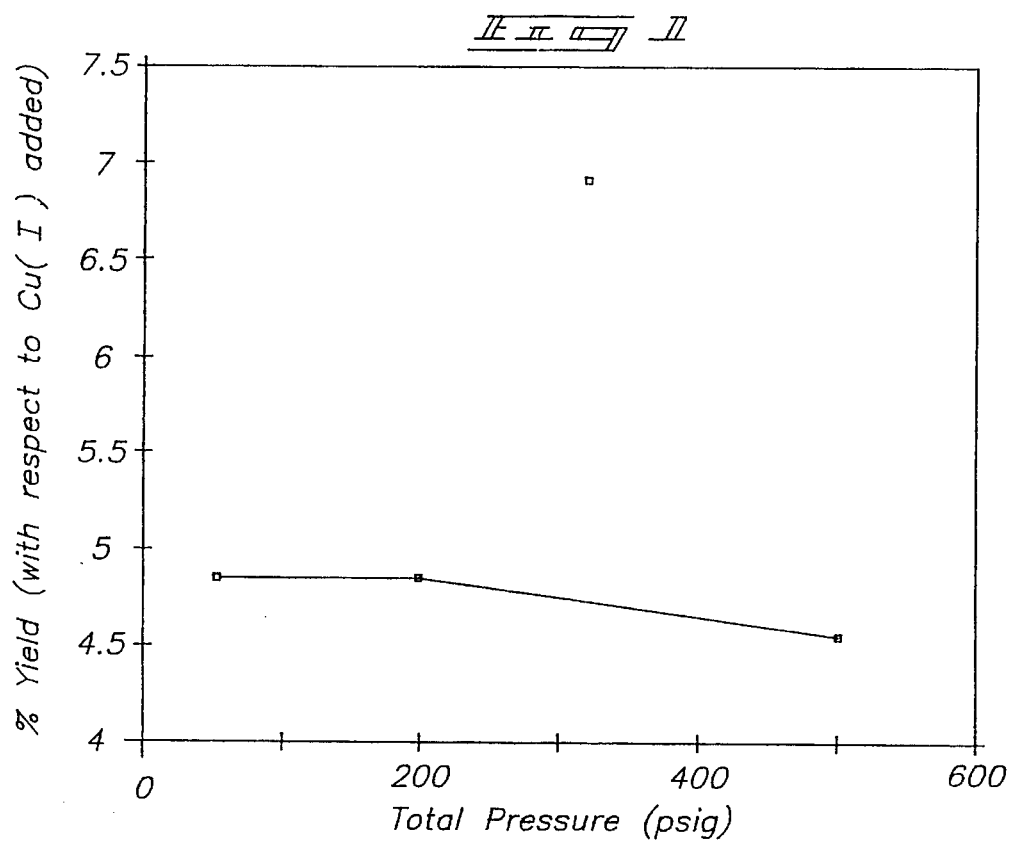
FIG. 1 is a graph of methyltrifluoroacetate yield as a function of total pressure.

This disclosure of the invention is submitted in furtherance of the constitutional purposes of the U.S. Patent Laws "to promote the progress of science and useful arts" (Article 1, Section 8).

In accordance with the invention, a method is provided for selectively oxidizing an organic compound in a single vessel. In one aspect of the invention, the invention comprises:

combining in a single vessel an organic compound, an acid solution in which the organic compound is soluble, a compound containing two oxygen atoms bonded to one another, and a metal ion reducing agent capable of reducing one of the oxygen atoms of the compound containing two oxygen atoms bonded to one another, and thereby forming a mixture; the acid solution comprising $H^+$ion and an acid counter ion, the organic compound having a carbon atom bonded to a hydrogen atom; and maintaining the mixture at an effective temperature and effective pressure for a sufficient amount of time to, a) reduce one of the oxygen atoms in the compound containing two bonded oxygen atoms with the metal ion reducing agent, b) oxidize the metal ion reducing agent to a higher valence state, and c) bond the acid counter ion to the carbon atom of the organic compound in place of the hydrogen atom thereby producing an oxidized organic compound, preferably and most typically an ester. In most instances, the bonded acid counter ion will have a stabilizing effect by rendering the carbon atom bonded thereto substantially nonreactive to further oxidation within the mixture. The sufficient amount of time might be from one second to twelve hours, with from five minutes to twelve hours expected to be typical.

The reaction is understood to occur by a reduction of the compound containing the two oxygen atoms bounded to one another by reducing one of such oxygen atoms with the metal ion reducing agent. In some instances, the metal ion reducing agent will sever the oxygen-oxygen bond. In others, such bond will remain intact with one of the oxygens being more electrophilic than the other. Such reactions will have the effect of oxidizing the metal ion reducing agent to a higher valence state, and produce an oxygen containing intermediate capable of oxidizing the organic compound.

The oxygen containing intermediate is reacted with the organic compound, and not with the acid solution, to oxidize the organic compound into an oxidized organic intermediate and form water. The oxidized organic intermediate will have had at least one of its carbon atoms oxidized by action with the oxygen containing intermediate. The oxidized organic intermediate is reacted with the acid counter ion and higher valence state metal ion to bond the acid counter ion to the oxidized carbon atom, and thereby produce a quantity of ester incorporating the organic intermediate and acid counter ion. Olefins may as well be produced, which would typically be converted to esters.

The oxidized organic intermediate also reacts with the higher valence state metal ion and water to produce a quantity of alcohol, with the quantity of ester being greater than the quantity of alcohol. Bonding of the acid counter ion with the carbon atom renders such carbon atom less reactive with the oxygen containing intermediate in the mixture than is the alcohol with the oxygen containing intermediate. The higher valence state metal ion can be converted to a low valence state for oxidizing more of the organic compound.

It is expected that the above method will not only oxidize the carbon atom in the oxidized organic intermediate, but also functionalize it as well. In one aspect, the carbon atom could be functionalized to a radical. In another aspect, the particular carbon atom might be functionalized by removal of a hydride ion. In yet another example, an electron might be withdrawn followed by loss of a proton.

For example where the organic compound being oxidized is propane ($H_3C$—$CH_2$—$CH_3$), at least one carbon atom would be oxidized for example to define a radical, such as $H_3C$—$CH\cdot$—$CH_3$. The carbon atom which has been converted to $C\cdot$ would provide a link for ultimately bonding the acid counter ion thereto to form the ester. Such carbon atom would be substantially nonreactive to further oxidation within the mixture upon bonding with the acid counter ion. For long chain or cyclic hydrocarbons, it is expected that stabilization of the bonded carbon atom will as well have a stabilizing effect on adjacent (neighboring) carbon atoms towards oxidation.

Preferably, the acid solution comprises a fully fluorine substituted carboxylic acid, such as trifluoroacetic acid. Other acids may be used such as, by way of example only, sulfuric acid, trifluoromethane sulfonic acid, acetic acid, halogenated carboxylic acids and mixtures thereof. Additionally, the acid solution could include cosolvents such as, by way of example only, methylsulfone, trimethylene sulfone, acetonitrile, fluorinated ethers, fluorinated alcohols, fluorinated ketones and fluorinated hydrocarbons. Where carboxylic acid is used, it may be desirable to include the anhydride of the specific carboxylic acid to enhance end-product selectivity by minimizing free water production.

The compound containing two oxygens bonded to one another could simply be molecular oxygen gas, peroxides or other such compounds. Example metal ion reducing agents include Cu(I), Cr(II), V(II), and Ti(III). The described metal ion reducing agent might also be comprised of combinations of metal ions, especially for peroxidic oxidants. Here, one metal would serve to reduce the compound containing two oxygen atoms and generate the electrophilic oxidizing intermediate, while the other metal ion would oxidize the organic intermediate. One desirable feature would be that the reduced form of the second metal ion be readily oxidized by the oxidized form of the first metal ion so that a redox chain reaction is propagated. Possible ion combinations would include, Ti(III)/Cu(II); V(II)/Cu(II); Cu(II)/Cr(II); Fe(II)/Cu(II); and U(IV)/Cu(II).

It is anticipated that the invention will be usable with a very wide range of organic compounds to produce selected oxidation products.

The stabilization of the ester by the acid counter ion in such a way that the ester is less reactive with the oxygen containing intermediate than is the alcohol is an important feature of the invention. In prior art oxidation processes, alcohol presence is undesirable and leads to poor selectivity of end products. This is due to a tendency of the alcohol to be further oxidized. Accordingly, alcohol formation within the oxidation process itself is preferably minimized. The same preference exists in the inventive process of this disclosure. Yet, it is a feature of this invention to create an ester product which is more stable than the corresponding alcohol towards further oxidation, and thereby achieve a selective end product and at the same time minimize alcohol formation during the oxidation. The goal is to maximize ester formation and minimize alcohol formation.

Where olefins are formed, an ester, olefin and alcohol mixture is produced. The olefins would be formed by reacting the oxidized organic intermediate with the higher valence state metal ion to produce a quantity of olefin. In such instances, the acid counter ion incorporated in the ester renders the carbon atom bonded thereto less reactive with the oxygen containing intermediate than are both the alcohol and olefin with the oxygen containing intermediate. Preferably, the acid to water ratio is determined by experiment, or empirically, and maintained such that the quantity of ester produced predominates over the quantity of olefin and alcohol which are produced.

An example method in accordance with the invention utilizing Cu(I) and $O_2$ comprises:

reacting Cu(I) with $O_2$ and $H^+$ in solution to oxidize the Cu(I) to Cu(II) and form hydroperoxyl radical;

reacting hydroperoxyl radical with Cu(I) and $H^+$ in solution to oxidize Cu(I) to Cu(II) and form $H_2O_2$;

reacting $H_2O_2$ with Cu(I) to form $OH^-$, Cu(II) and hydroxyl radical;

reacting hydroxyl radical with an organic compound in solution to form $H_2O$ and an organic radical; and reacting the organic radical with Cu(II) and the acid counter ion to combine the counter ion and organic radical into an ester compound. Cu(I) can be generated from reaction of Cu(0) and Cu(II), or by other methods, as will be more fully described below.

The following pathway in accordance with the above example method employing Cu(I), $O_2$ and a solution of trifluoroacetic acid is illustrated for methane oxidation by equations 1–6 below:

$$Cu(I) + O_2 + H^+ \rightarrow Cu(II) + HO_2\cdot \qquad (1)$$

$$HO_2\cdot + Cu(I) + H^+ \rightarrow H_2O_2 + Cu(II) \qquad (2)$$

$$H_2O_2 + Cu(I) \rightarrow HO\cdot + HO^- + Cu(II) \qquad (3)$$

$$HO\cdot + CH_4 \rightarrow H_3C\cdot + H_2O \qquad (4)$$

$$H_3C\cdot + Cu(II) + CF_3CO_2^- \rightarrow (CH_3)Cu(O_2CCF_3)^+ \qquad (5)$$

$$(CH_3)Cu(O_2CCF_3)^+ \rightarrow CF_3CO_2CH_3 + Cu(I) \quad (6)$$

This chemistry involves the generation of hydroxyl radical from $O_2$ and Cu(I) in trifluoroacetic acid (equations 1–3), the reaction of hydroxyl radical with methane to form methyl radical (equation 4), the Cu(II)-mediated formation of $(CH_3)Cu(O_2CCF_3)^+$ (equation 5), and subsequent formation of methyltrifluoroacetate (equation 6). The electron-withdrawing trifluoroacetate group makes methyltrifluoroacetate less reactive than methane and methanol with hydroxyl radical. Because it is readily hydrolyzed to methanol (in a separate process step), methyltrifluoroacetate (the acid counter ion organic derivative) is a useful oxidation-stopping intermediate.

In a commercial process the oxidized metal ion, such as Cu(II), produced by the overall process could be electrolytically converted (reduced) to its lower valence state, such as Cu(I), which is the active metal ion reducing agent. Alternate methods could as well be used. Additionally, Cu(II) could be recycled by conversion to a lower valence state for oxidizing more of the organic compound.

The reaction of the oxidized organic intermediate with the acid counter ion and higher valence state metal ion to bond the acid counter ion to the oxidized carbon atom could proceed along one of several pathways. One of such pathways is described above with respect to equations 5 and 6. Here, the oxidized carbon atom is in the form of a radical, and couples along with the counter ion to the higher valence state metal ion. Subsequently, the organic/metal/counter ion complex dissociates to the desired ester product, thereby stabilizing the particular carbon atom bonded to the counter ion making such carbon atom substantially nonreactive to further oxidation within the mixture.

An alternate pathway would have the metal ion reacting with the oxidized organic intermediate to produce an olefin. Thereafter, the olefin would be solvolyzed to the ester. Alternately, the olefin could be extracted into the organic phase.

Yet another pathway, where high water content was present, might first produce an alcohol, which would then be esterified into the ester in the acid solution.

Diesters as well might be formed. For example, a feed stock of propene might first be solvolyzed to propyltrifluoroacetate. Such a compound might then be oxidized within the mixture to bis (1,2-trifluoroacetoxy) propane. Bonding of the counter ion with each respective carbon atom would stabilize such carbon atom to be substantially nonreactive to further oxidation within the particular mixture.

Several experiments under a variety of conditions were conducted to test the combined chemistry of equations 1–6. Cu(I) was added both as a solid in the form of $Cu_2O$ and as a solution of $CuO_2CCF_3$ to solutions containing $Cu(O_2CCF_3)_2$ under a methane/oxygen atmosphere. The solvent containing Cu(I) was anhydrous trifluoroacetic acid containing trifluoroacetic anhydride. The solvent for the Cu(II) solution was anhydrous trifluoroacetic acid or a mixed solvent containing trifluoroacetic acid and either water or acetonitrile. Acetic acid was also used as the solvent in a series of runs. Cu(II) was introduced as basic copper carbonate which reacts with the acid to form the salt and $CO_2$. Experiments were conducted at total pressures ranging from atmospheric to 500 psig and at temperatures between 20° and 70° C. Also, cyclohexane rather than methane was used in two experiments. Analytical and other experimental details can be found in the Experimental Conditions section which follows.

Figure 2:
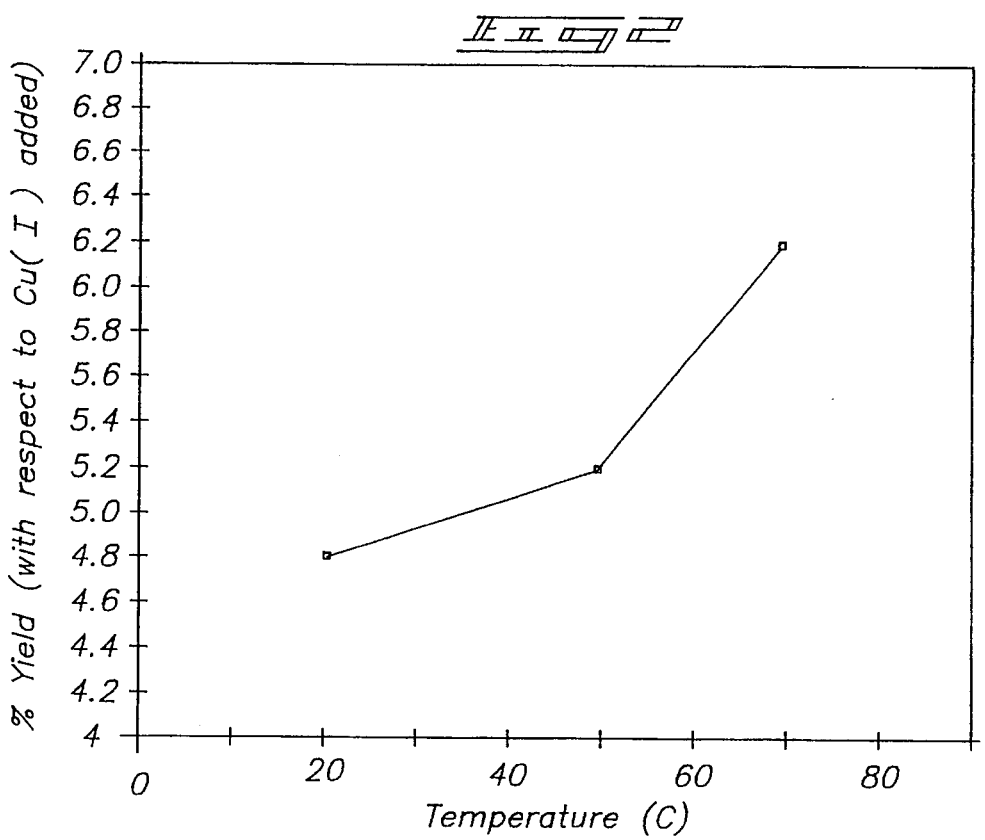
FIG. 2 is a graph of methyltrifluoroacetate yield as a function of temperature.
Figure 3:
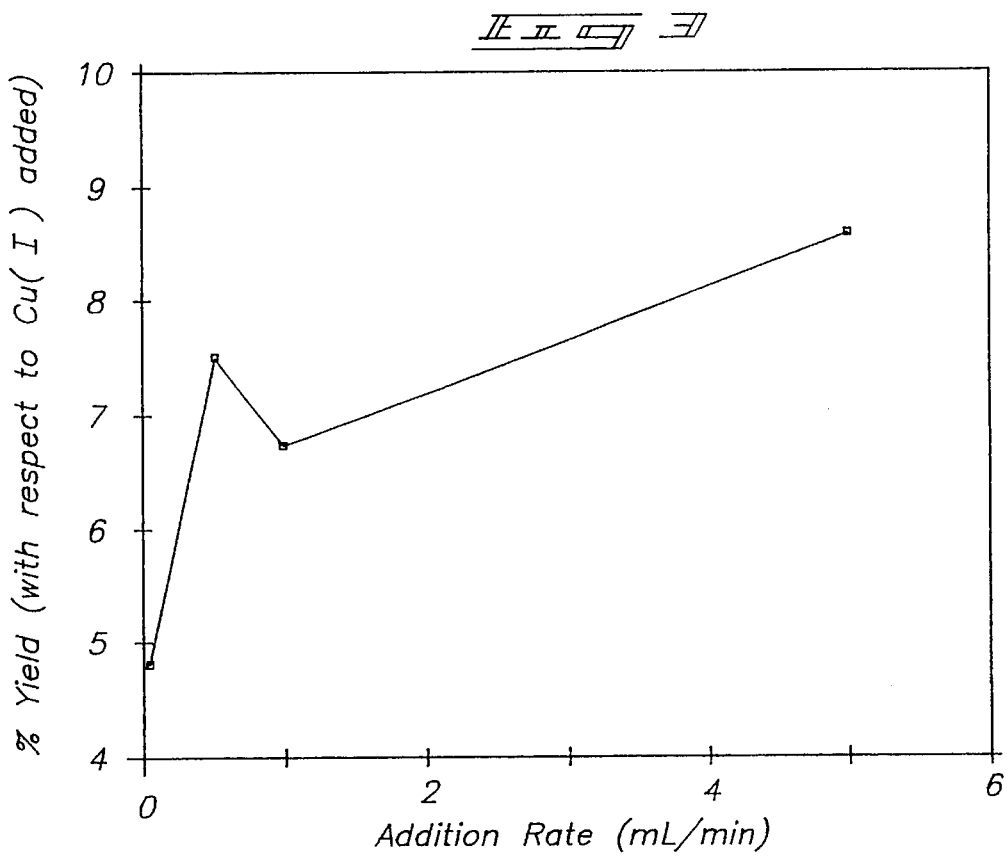
FIG. 3 is a graph of methyltrifluoroacetate yield as a function of Cu(I) addition rate.

A series of experiments was conducted in which a solution of $CuO_2CCF_3$ in trifluoroacetic acid was added to $Cu(O_2CCF_3)_2$ dissolved in the same acid containing 10% (v/v) $H_2O$. The results, in terms of percent yield of methyltrifluoroacetate with respect to the amount of Cu(I) added (for the stoichiometry of equations 1–6 above), for pressure, temperature, and addition rate variations are given in Tables 1–3, and illustrated in FIGS. 1–3, respectively.

TABLE 1

Methyltrifluoroacetate Yield as a Function of Pressure[a].

| Run # | Total Pressure (psig) | % Yield |
|---|---|---|
| C4 | 50 | 4.88 |
| C1 | 200 | 4.87 |
| C2 | 320[b] | 6.85 |
| C3 | 500 | 4.56 |

[a] 2 ml/h solution addition rate, 20° C., 7.5 psig $O_2$
[b] Gas leak reduced pressure from 500 to 320 psig

TABLE 2

Methyltrifluoroacetate Yield as a Function of Temperature[a].

| Run # | Temperature (°C.) | % Yield |
|---|---|---|
| C1 | 20 | 4.87 |
| C5 | 50 | 5.35 |
| C6 | 70 | 6.28 |

[a] 2 ml/h solution addition rate, 200 psig initial pressure

TABLE 3

Methyltrifluoroacetate Yield as a Function of Addition Rate[a].

| Run # | Addition Rate (ml/min) | % Yield |
|---|---|---|
| C1 | 0.033 | 4.87 |
| C7 | 0.333 | 7.51 |
| C8 | 1.0 | 6.75 |
| C9 | 5.0 | 8.73 |

[a] 200 psig, 20° C.

Pressure experiments were conducted with 7.5 psig $O_2$, with the balance being $CH_4$. From Table 1 and FIG. 1 it is seen that pressure within the range studied does not have a great effect in yield. The result of run #C2, however, is noteworthy. In this run, a leak dropped the pressure from 500 to 320 psig before it was discovered. The effect of the leak was to lower the oxygen partial pressure to about 4.8 psig (and the $CH_4$ partial pressure to 315.2 psig). Although the effect of oxygen pressure was not specifically studied, this result may indicate that a lower $O_2$ pressure may give a higher product yield (by a factor of 1.5 in this case).

Yields increased moderately with increasing temperature. The yield at 70° C. is about 1.3 times that at 20° C. A larger effect is seen with increasing Cu(I) solution addition rate. The yield at the fastest rate (5ml/min) is nearly double that at the slowest rate (2 ml/hour), and may be even higher at faster addition rates or at higher Cu(I) solution concentrations.

The observation that yields increased with increasing addition rate is consistent with speculation that yields increase at lower $O_2$ partial pressures, since the dissolved $O_2$ concentration is likely to be lower at faster Cu(I) feed rates. At relatively high $O_2$ concentrations, the generation of hydroxyl radicals by equation 3 may be inefficient because most of the Cu(I) is scavenged by the reactions of equations 1 and 2. Once hydroxyl radical is generated, conversion to ester product is efficient as indicated by the insensitivity of yield to $CH_4$ pressure. Presumably the competing reaction (reduction of hydroxyl radical to hydroxide by reaction with Cu(I)) is negligible because the Cu(I) concentration is low under the conditions of these experiments. At higher Cu(I) or lower $O_2$ concentrations, this reaction will be more important. Ligand transfer oxidation (equations 5 and 6) is apparently a facile process in this system since reduction of the Cu(II) concentration by a factor of four had no effect on product yield (in experiments in which solid $Cu_2O$ was the source of Cu(I) and at 200 psig).

The stability of methyltrifluoroacetate to further reaction in this system was demonstrated by running the reaction in the presence of added ester. Ester was added to the initial reaction solution to bring its concentration to about that of $CH_4$ at 192.5 psig (200 psi total pressure, conditions identical to run #C8). The final reaction solution was found to contain more ester than originally added. The excess produced corresponded to a yield of 8.9%. This was comparable to the yield in the control run #C8 (6.75%), indicating that reaction of hydroxyl radical with methane is favored over reaction with methyltrifluoroacetate.

Other experiments using solid $Cu_2O$ were run to investigate the effects of pressure, mixed solvents, and anion variations. Table 4 summarizes results of experiments conducted at room temperature under an atmosphere consisting of 80% $CH_4$, 10% $O_2$, and 10% inert gas (primarily $N_2$).

TABLE 4

Product Yield[a] for Methane Conversion at Atmospheric Pressure for Addition of Cu(I) as a Solid or in Solution.

| Solid Cu(I) Addition | | Cu(I) Solution Addition |
|---|---|---|
| Anhydrous | 10% $H_2O$ | 10% $H_2O$ |
| 2.46 | 5.15 | 1.93 |

[a]% yield based on total Cu(I) added

Yields in acid solution containing 10% water were higher than those in solutions maintained anhydrous by the addition of trifluoroacetic anhydride. Hydrolysis of the methyl ester apparently does not occur to an appreciable extent in the aqueous acid solution. This has important implications in scale-up of the process since rigorous removal of product water will not be a critical requirement. For Cu(I) solution addition under identical conditions, the yield was lower. This may be a result of differing local Cu(I) concentrations or surface reactions and indicates that solid and solution results are not directly comparable.

The effect of pressure on product yield in experiments in which solid Cu(I) was used under anhydrous conditions is shown in Table 5.

TABLE 5

Product Yield[a] for Methane Conversion at Elevated Pressure for Solid Addition of Cu(I) Under Anhydrous Conditions.

| | Gas Composition (psig) | | | |
|---|---|---|---|---|
| Run # | $CH_4$ | $O_2$ | $CO_2$ | % Yield |
| 4 | 192.5 | 7.5 | 0 | 0.30 |
| 5 | 492.5 | 7.5 | 0 | 0.35 |
| 17 | 169.5 | 7.5 | 32.5 | 0.28 |

[a]% yield based on total Cu(I) added

Yields are much lower than at atmospheric pressure (Table 4). Also, increasing pressure had no effect on product yield, consistent with the pressure experiments in which a Cu(I) solution was added to an aqueous acid solution of Cu(II) (Table 1). These observations again indicate that the yield-limiting process does not involve the reaction of oxidant with methane. Added $CO_2$ has no effect on product yield (run #17).

Results of experiments investigating mixed solvents containing acetonitrile and trifluoroacetic acid, and solutions containing trifluoromethanesulfonic acid, are shown in Table 6.

TABLE 6

Product Yield[a] for Methane Conversion in Acetonitrile Solutions for Solid Addition of Cu(I)[b] Under Anhydrous Conditions.

| | % Yield | |
|---|---|---|
| ml $CH_3CN$ | without $CF_3SO_3H$ | with $CF_3SO_3H$[c] |
| 1 ml (0.019 moles) | 0.06 | 0.38 |
| 6 ml (0.12 moles) | trace | trace |

[a]% yield based on total Cu(I) added
[b]0.0124 moles Cu(I), 0.00276 moles Cu(II)
[c]0.017 moles (1.5 ml)

Although product is formed, acetonitrile clearly inhibits its formation. Trifluoromethanesulfonic acid promotes product formation at low acetonitrile concentrations, but does not overcome the inhibition at higher concentrations. Addition of $CF_3SO_3H$ to $CF_3CO_2H/H_2O$ solutions may also result in higher product yields.

In other experiments, CuCl was tested as a Cu(I) source at 200 psig total pressure. Only a trace of product was obtained due to the low solubility in the solvents (both anhydrous and aqueous $CF_3CO_2H$). Runs in acetic acid with solid $Cu_2O$ at 200 psig gave methyl acetate. However, a control run under a nitrogen/oxygen atmosphere (no methane) also gave a good yield of product, indicating that decarboxylation of the acid occurred.

Activation of cyclohexane was also investigated in two experiments. Under anhydrous conditions, slow addition of Cu(I) dissolved in $CF_3CO_2H$ to a solution of Cu(II) dissolved in $CF_3CO_2H/C_6H_{12}$ in air and gave a 17% yield of cyclohexyltrifluoroacetate. A 19.2% yield of this ester was obtained when solid $Cu_2O$ was stirred in the Cu(II) solution under a 100% $O_2$ atmosphere. The yields are comparable even under widely varying conditions. Also, the yields are higher than for methane activation, probably due primarily to easier activation of a secondary hydrogen atom, aided by a higher solution concentration of cyclohexane (0.4M compared to about 0.01M).

Such experiments demonstrate direct methane conversion at atmospheric pressure and room temperature. Furthermore, the product methyltrifluoroacetate is specifically produced, readily hydrolyzed to methanol, and volatile.

The volatility of methyltrifluoroacetate (bp 43° C.) suggests that a continuous process may be possible in which the ester is distilled from the reaction solution and hydrolyzed to methanol in a second reaction vessel. The overall reaction requires the generation of Cu(I), since two equivalents are used for each mole of ester produced. This may be best accomplished by the electrochemical reduction of Cu(II), which is produced in the scheme according to equations. 1–3. Assuming 10% efficiency in Cu(I) use and $0.04/Kwh, the cost for electricity per pound of methanol produced would be about $0.027.

Experimental Conditions

Experiments at atmospheric pressure were conducted in a glass apparatus consisting of a 2-necked flask connected to a 2-liter gas reservoir and a gas buret. The gas buret, filled with mercury, permitted the measurement of gas uptake and the maintenance of 1 atmosphere pressure within the system. In a typical experiment under anhydrous conditions, 0.33 g $CuCO_3 \cdot Cu(OH)_2 \cdot H_2O$ was dissolved in 25 ml $CF_3CO_2H$. The apparatus was then purged with an 80% $CH_4$, 10% $O_2$, 10% inert gas mixture prepared from compressed natural gas and oxygen using flowmeters. Solid $Cu_2O$ (0.89 g) and $(CF_3CO)_2O$ (12 ml) were added and purging continued until the outlet flow had the same composition as the inlet feed. The purge was then stopped, the reactor sealed, and stirring commenced. Gas buret readings were taken throughout the course of the reaction, which ran for about two days. Experiments in aqueous acid solution were run similarly, except that the Cu(II) solvent consisted of 36 ml acid and 4 ml $H_2O$ and no anhydride was added. Cu(I) dissolved much more slowly in this medium and runs typically required about 5 days (although a small amount of Cu(I) was often still present when reactions were worked up).

Experiments under pressure using solid $Cu_2O$ were run in a 300 ml autoclave. After charging the reactor with all reagents (prepared as for the atmospheric runs), purging was accomplished by 3 pressurization/vent cycles using 200 psig $CH_4$. The autoclave was then charged with $CH_4$ followed by $O_2$ and stirring commenced. Pressure readings and gas samples were taken throughout the run. Experiments were complete overnight. Experiments involving addition of Cu(I) in solution were carried out similarly except that an anhydrous $Cu_2OCCF_3$ solution in $CF_3CO_2H$ was pumped out of a buret under nitrogen into the autoclave with use of a high pressure Pulsa-Feeder pump.

Gas samples were analyzed on a Carle series 400 AGC gas chromatograph for $CH_4$, $O_2$, $N_2$, and $CO_2$ content. Other gas components were analyzed, when necessary, on a GS-Q (Megabore) column in a HP 5890 gas chromatograph.

At the conclusion of a run, the final solution was weighed and a portion cryogenically distilled to remove copper salts. A known weight of the liquid was then combined with a known volume of a standard $CH_2Cl_2/CF_3CO_2H$ solution and analyzed by gas chromatography. Response factors were determined for methyltrifluoroacetate relative to $CH_2Cl_2$ as standard. The columns and instruments used were a GS-Q (Megabore) column and SP 1000 on Carbopack B in a HP 5992 gas chromatograph/mass spectrometer system. The identity of the product as methyltrifluoroacetate was established by comparison of gc retention times and mass spectrometer fragmentation patterns with an authentic ester sample (acquired from Aldrich Co. of Milwaukie, Wis.).

Cu(I) from Cu(0) and Cu(II)

Cu(I) is producible by reaction Cu(0) and Cu(II). For example, C. L. Jenkins et al. *J. Amer. Chem. Soc.*, (1972), 94, 843, 855 reports the preparation of cuprous triflate by the reaction of cupric triflate with copper metal in deoxygenated acetonitrile/triflic acid solution.

$$Cu(0) + Cu(II) \rightarrow 2 Cu(I) \quad (7)$$

In our experiments, UV/Vis spectra show that cupric trifluoroacetate does not react with copper metal after stirring 64 hours in deoxygenated trifluoroacetic acid containing 10 volume per cent $H_2O$. The blue color did not dissipate and the copper metal did not dissolve after another week of stirring. In contrast, solutions exposed to the atmosphere did react to five more intensely blue solutions. The Cu(II) concentration increased to give more intensely blue solutions. The Cu(II) concentration increased presumably by the sequence shown in equation 8. The increase was about that predicted by the conversion of copper metal to Cu(II).

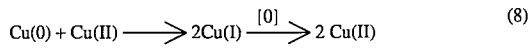

$$Cu(0) + Cu(II) \longrightarrow 2Cu(I) \xrightarrow{[O]} 2 Cu(II) \quad (8)$$

Figure 4:
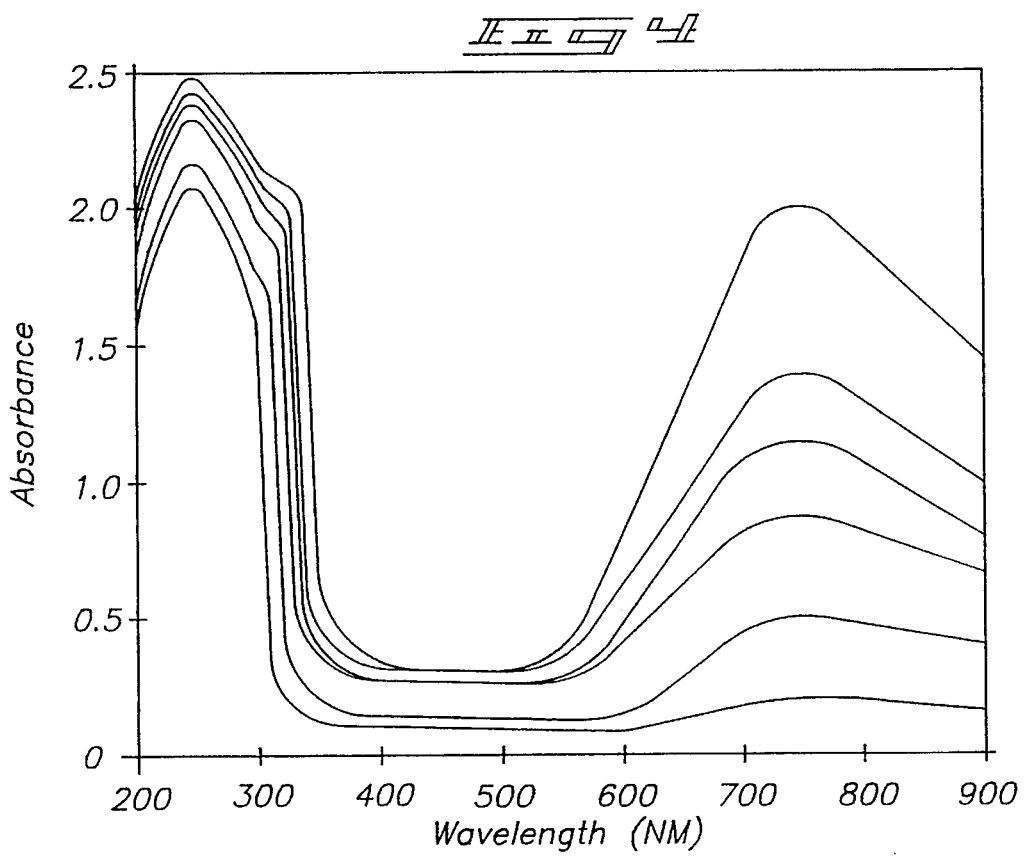
FIG. 4 illustrates spectral changes in the course of the reaction of copper metal with Cu(II) in 10% v/v $H_2O$/trifluoroacetic acid.

FIG. 4 shows spectra taken during the course of this reaction. A baseline increase resulting from the precipitation of a white solid was observed. This precipitate formed despite the use of distilled acid and $HNO_3$-washed copper metal.

Figure 5:
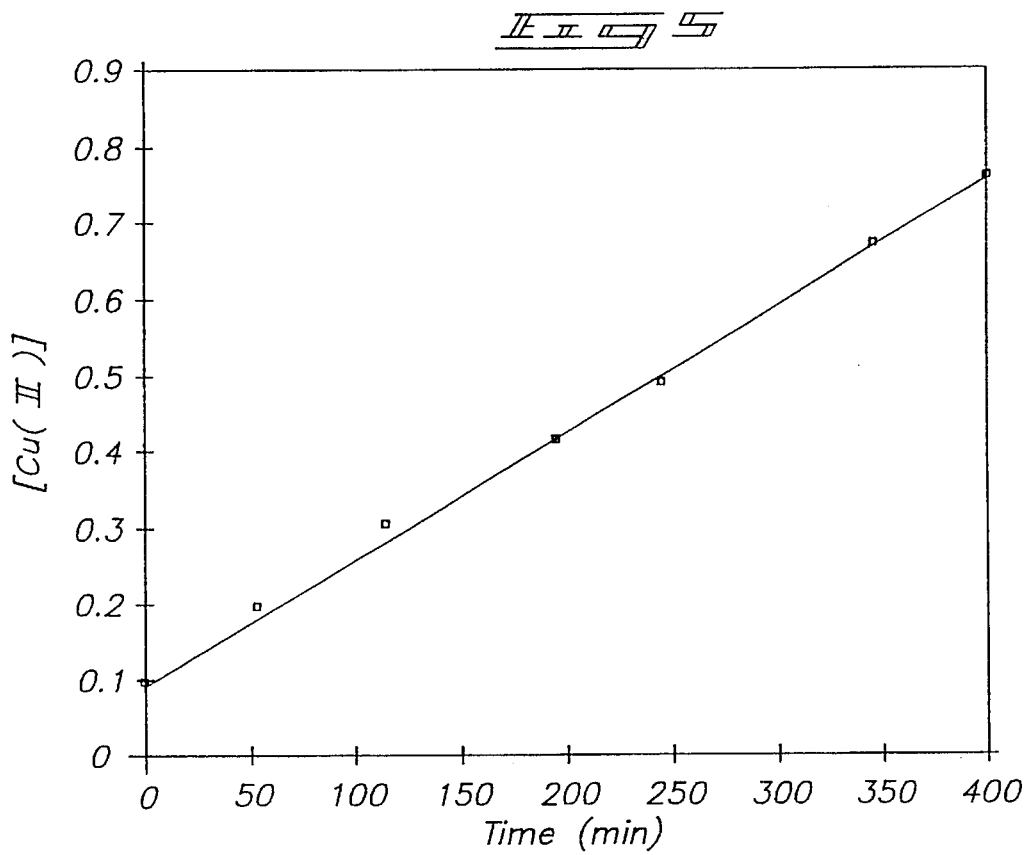
FIG. 5 illustrates Cu(II) concentration increase in the course of the reaction of copper metal with Cu(II) in 10% v/v $H_2O$/trifluoroacetic acid.

FIG. 5 shows that the Cu(II) concentration increase is linear with reaction time, an unexpected result which suggests that the effect of decreasing metal surface area is offset by the increasing Cu(II) concentration. Under the experimental conditions, the rate of Cu(0) dissolution is $1.18 \times 10^{-3}$ g/min and the rate of Cu(I) generation is $3.71 \times 10^{-5}$ moles/min.

The white precipitate which formed was analyzed by infrared spectroscopy. In a NaCl matrix, broad absorbances were observed at 730 and 500 $cm^{-1}$. No absorbances for trifluoroacetate were observed. The absorbances do not correspond to either CuO (500 $cm^{-1}$ only, KBr pellet) or $Cu_2O$ (625, 425 $cm^{-1}$, CsI pellet). In addition, the material reacted with solid KBr, indicating that it is a strong oxidant. The chemical composition of this material was not determined, but the possibility exists that it contains Cu(III). Also, the formation of Cu(III), if by reaction of hydroxyl radical with Cu(II), represents inefficiency in hydroxyl radical utilization. On the other hand, this material has the potential to oxidize hydrocarbons.

The use of the Cu(O)/Cu(II)/$O_2$ system to generate hydroxyl radical was tested using cyclohexane as substrate. In the two experiments conducted, the expected oxidation product, cyclohexyltrifluoroacetate, was formed in 20.3 and 30.8% yield based on copper metal added. The higher yield was obtained when a five-fold increase of Cu metal was used. These yields compared favorably to those found earlier (17–19%) using either solid or dissolved $Cu_2O$ as the Cu(I) source.

Both experiments with copper metal deposited the white precipitate. During the course of the second experiment, solution samples were taken for analysis. Cyclohexene was found to be the major reaction product (ester/olefin=0.2) which slowly reacted with trifluoroacetic acid to form cyclohexyltrifluoroacetate. Thus, elimination of cyclohexene from a cyclohexyl-copper complex is the predominant reaction pathway under our conditions.

Figure 6:
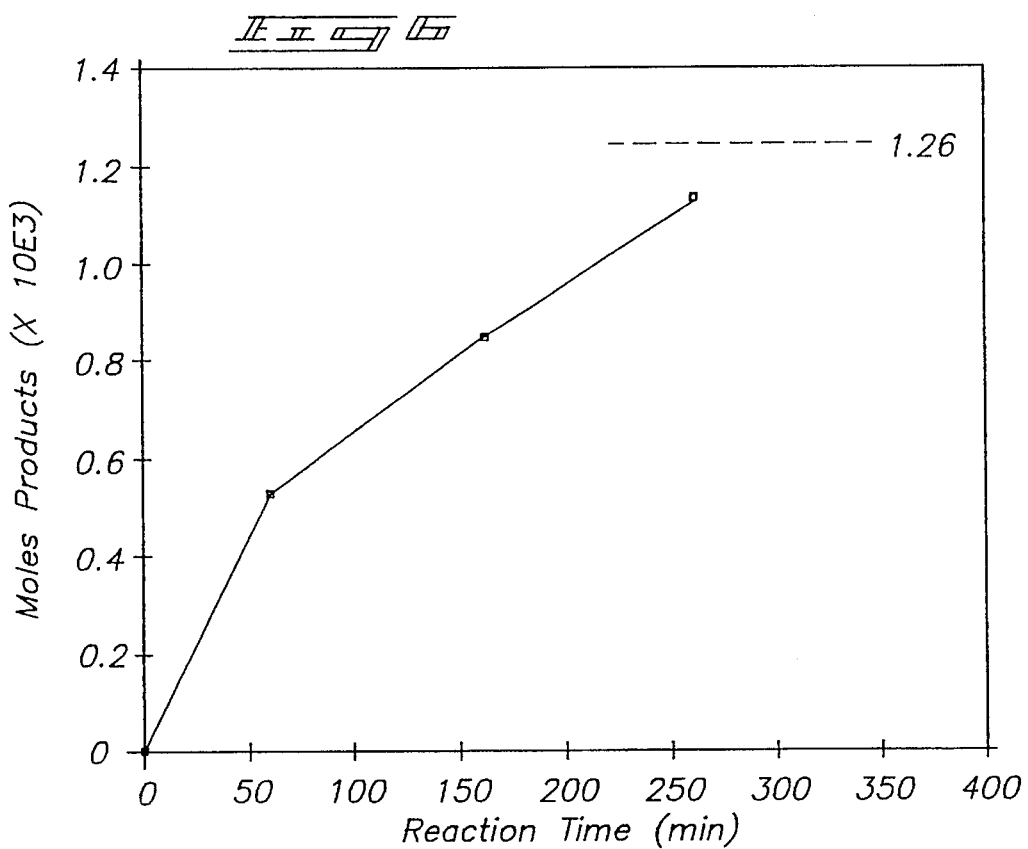
FIG. 6 illustrates moles of products formed as a function of reaction time in the oxidation of cyclohexane by a Cu(0)/Cu(II)/$O_2$ system.

FIG. 6 shows a plot of total product formation as a function of reaction time. The final yield is indicated by the horizontal dotted line at $1.26 \times 10^{-3}$ moles. This yield represents conversion of 11% of the cyclohexane. However, mass balance only accounted for 93% of the starting material.

Experimental Conditions

Copper dissolution experiments were conducted by stirring copper metal (0.507 g, $7.98 \times 10^{-3}$ moles) in 10 ml of a $7.53 \times 10^{-2}$M Cu(II) solution prepared by adding cupric carbonate (0.18 g) to 18 ml trifluoroacetic acid and 2 ml water. The change in Cu(II) concentration was monitored by UV/Vis spectrophotometry using a 1 mm cell in a Perkin-Elmer Lambda Array 3840 spectrophotometer.

In cyclohexane oxidation experiments, copper metal (0.049 to 0.26 g) was added to 40 ml of a $7.25 \times 10^{-2}$M Cu(II) solution (10% $H_2O$ in trifluoroacetic acid) containing 1.5 ml cyclohexane in a round bottom flask fitted with a condenser. Air was the oxidant. Samples were withdrawn for analysis during the course of one experiment. Analyses were performed by gas chromatography using a HP 5830A gas chromatograph. Solution samples containing octane as internal standard were injected directly onto a packed column of 1% $H_3PO_4$ and 10% SP-1200 on 80/100 Chromasorb WAW (Supelco). This column allowed for analysis of cyclohexane, cyclohexene, and cyclohexyltrifluoroacetate.

Rate of Reactions and Reactant Mixture Concentrations

Organic compounds undergo consecutive oxidation reactions to a series of increasingly oxidized products. The first-formed product is difficult to obtain in good yield because its reactivity is usually greater than that of the starting compound. Limiting secondary oxidation in organic oxidation reactions can be accomplished either by carrying out the reaction under low conversions conditions or by stabilizing the first primary product to further oxidation. In either case, the objective is to maximize the rate of oxidation of reactant relative to the first-formed product (equation 9), i.e., maintain $R_{rel}$ as large as possible.

$$\frac{\text{Rate of Reactant oxidn.}}{\text{Rate of Product oxidn.}} = \frac{k_{react} \, [\text{react}]}{k_{prod} \, [\text{prod}]} = R_{rel} \quad (9)$$

$R_{rel}$ is a function of time and will be large at the beginning of the oxidation because [prod] is very small. As the reaction progresses, [prod] will tend to increase and $R_{rel}$ will decrease. $R_{rel}$ should be significantly greater than one (1) throughout the reaction in order to provide selective oxidation of organic compounds to esters. More specifically, $R_{rel}$ should preferably be at least 10, and most preferably greater than 100. To keep $R_{rel}$ at least 10 and most preferably greater than 100, [prod] can be decreased by removal from the reactor (low conversion) or by conversion to a less reactive compound (stabilization).

Where the reaction product includes an alcohol, conversion to its ester in the reactor is one method of stabilization because esters are less reactive than their corresponding alcohols. This method is convenient because the ester can be subsequently hydrolyzed back to the alcohol in a separate reactor. The conversion of alcohols to esters is illustrated in equation 10 and the equilibrium expression is shown in equation 11.

$$\text{alcohol} + \text{acid} \rightleftharpoons \text{ester} + \text{water} \quad (10)$$

$$K_{eq} = \frac{[\text{ester}] \, [\text{water}]}{[\text{alcohol}] \, [\text{acid}]} \quad (11)$$

The position of the equilibrium in equation 10 depends upon the concentrations of the acid and water as shown in equation 12.

$$\frac{[\text{acid}]}{[\text{water}]} = \frac{[\text{ester}]}{[\text{alcohol}] \cdot K_{eq}} \quad (12)$$

High [acid]/[water] ratios favor ester formation at the expense of alcohol. Conversely, low [acid]/[water] ratios will increase the alcohol concentration relative to ester.

Equation 13 derived by combining equation 11 with equation 9 for the case where alcohols (ROH) are desired from oxidation of a hydrocarbon (RH), shows clearly that $R_{rel}$ is directly proportional to [acid]/[water] ratios and the magnitude of the equilibrium constant for esterification (equations 10 and 11).

$$\frac{\text{Rate of } RH \text{ Oxidn.}}{\text{Rate of } ROH \text{ Oxidn.}} = R_{rel} = \frac{K_{RH} k_{eq}}{K_{ROH}} \cdot \frac{[\text{Acid}]}{[\text{water}]} \cdot \frac{[RH]}{[\text{Ester}]} \quad (13)$$

Therefore, for maximum production of ester, the water concentration should be minimized relative to the acid concentration.

Similar reasoning can be applied for the case where the product of the oxidation is an olefin. This product may also be stabilized towards further oxidation as an ester formed by solvolysis, such as shown in equation 14 where "A" is the acid counter ion. For example, when the acid is trifluoroacetic acid, "A" would be $CF_3CO_2$. Conversion of the olefin to the more stable ester increases $R_{rel}$. Additionally, in a separate reactor, pyrolysis of the ester could regenerate olefin by reversal of equation 14.

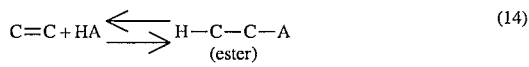

$$C=C + HA \rightleftharpoons \underset{(\text{ester})}{H-C-C-A} \quad (14)$$

The [acid]/[water] ratio will determine the extent of hydrolysis of the ester to the more reactive alcohol. Again for maximum yield, a high [acid]/[water] ratio is desired. Also an acid stable to the oxidation conditions and having a sufficiently large $K_{eq}$ should be used.

From the foregoing, it is apparent that the optimum conditions would be anhydrous. This requires the inclusion of drying agents such as acid anhydrides because water is produced in oxidations that use oxygen, hydrogen peroxide or organic hydroperoxides. Another advantage in using anhydrous conditions is that the organic hydrocarbons have greater solubilities. However, the metal ion reactants and catalysts will have lesser solubility in anhydrous media. Another concern when using anhydrides to assure anhydrous conditions is that peroxyacids may be intermediately formed and lead to destruction of the acid during the oxidation. Thus, in scaling up this process for industrial applications, the advantages of anhydrous conditions (maximum yields) will have to be weighed against the higher costs associated with maintaining anhydrous reaction conditions (anhydrides and acid loss). We have found encouraging yields of esters are produced even with a 2/1 molar ratio of trifluoroacetic acid to water. This finding and above analysis suggests that some water may be tolerable or even desirable for economic reasons.

While a detailed kinetic model may be formulated and used to determine the minimum tolerable [acid]/[water] ratio, a more convenient approach could be empirical determination. A series of oxidation experiments could be performed in which the starting [acid]/[water] ratio is decreased while the initial concentrations of the other reactants are not varied. By monitoring the extent of secondary oxidation as a function of conversion, the best ratio is chosen which maximizes product yield but minimizes over-oxidation.

In compliance with the statute, the invention has been described in language more or less specific as to methodical features. It is to be understood, however, that the invention is not limited to the specific features described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. A method of oxidizing a hydrocarbon compound in a single vessel comprising:

combining in a single vessel the hydrocarbon compound, an acid solution in which the hydrocarbon compound is soluble, a compound containing two oxygen atoms bonded to one another, and a reactant metal ion reducing agent capable of reducing one of the oxygen atoms of the compound containing two oxygen atoms bonded to one another, and thereby forming a mixture; the acid solution comprising $H^+$ ion and an acid counter ion;

reducing the compound containing the two oxygen atoms bonded to one another by reducing one of such oxygen atoms with the reactant metal ion reducing agent to, a) oxidize the reactant metal ion reducing agent to a higher valence state, and b) produce an oxygen containing intermediate capable of oxidizing the hydrocarbon compound;

reacting the oxygen containing intermediate with the hydrocarbon compound and not with the acid solution to oxidize the hydrocarbon compound in the acid solution into an oxidized hydrocarbon intermediate, the oxidized hydrocarbon intermediate having an oxidized carbon atom;

reacting the oxidized hydrocarbon intermediate with the acid counter ion and higher valence state metal ion to bond the acid counter ion to the oxidized carbon atom and thereby produce a quantity of an ester incorporating the hydrocarbon intermediate and acid counter ion;

reacting the oxidized hydrocarbon intermediate with the higher valence state metal ion and water to produce a quantity of alcohol, the quantity of ester being greater than the quantity of alcohol and the quantity of ester being less than or equal to a corresponding stoichiometric amount of the reactant metal ion reducing agent; and the acid counter ion incorporated in the ester rendering the carbon atom bonded to the counter ion less reactive with the oxygen containing intermediate in the mixture than is the alcohol with the oxygen containing intermediate.

2. The method of oxidizing a hydrocarbon compound of claim 1 further comprising recycling the higher valence state metal ion to a lower valence state for oxidizing more of the hydrocarbon compound.

3. The method of oxidizing a hydrocarbon compound of claim 1 wherein the acid solution comprises a fully fluorine substituted carboxylic acid.

4. The method of oxidizing a hydrocarbon compound of claim 1 wherein the hydrocarbon compound is selected from the group consisting of propane, methane and cyclohexane.

5. The method of oxidizing a hydrocarbon compound of claim 1 wherein the metal ion reducing agent comprises Cu(I).

6. The method of oxidizing a hydrocarbon compound of claim 1 wherein the compound containing two oxygen atoms is $O_2$.

7. The method of oxidizing a hydrocarbon compound of claim 1 wherein, the acid solution comprises a fully fluorine substituted carboxylic acid; and the metal ion reducing agent comprises Cu(I).

8. The method of oxidizing a hydrocarbon compound of claim 1 wherein, the acid solution comprises a fully fluorine substituted carboxylic acid;

the hydrocarbon compound is selected from the group consisting of propane, methane and cyclohexane; and the metal ion reducing agent comprises Cu(I).

9. The method of oxidizing a hydrocarbon compound of claim 1 wherein the hydrocarbon compound is an alkane.

10. The method of oxidizing a hydrocarbon compound of claim 1 wherein the hydrocarbon compound is a linear alkane.

11. The method of oxidizing a hydrocarbon compound of claim 1 wherein the hydrocarbon compound is a cyclic hydrocarbon.

12. The method of oxidizing a hydrocarbon compound of claim 1 wherein the hydrocarbon compound is non-aromatic.

13. The method of oxidizing a hydrocarbon compound of claim 1 wherein the metal ion reducing agent comprises Fe(II).

14. A method of oxidizing a reactant hydrocarbon compound in a single vessel comprising:

combining in a single vessel the reactant hydrocarbon compound, an acid solution in which the reactant hydrocarbon compound is soluble, a compound containing two oxygen atoms bonded to one another, and a reactant metal ion reducing agent capable of reducing one of the oxygen atoms of the compound containing two oxygen atoms bonded to one another, and thereby forming a mixture; the acid solution comprising $H^+$ ion and an acid counter ion, the reactant hydrocarbon compound having at least one carbon atom bonded to a hydrogen atom; and maintaining the mixture at an effective temperature and effective pressure for a sufficient amount of time to in the acid solution, a) reduce one of the oxygen atoms in the compound containing two oxygen atoms bonded to one another with the metal ion reducing agent, b) oxidize the reactant metal ion reducing agent to a higher valence state, and c) bond the acid counter ion to the one carbon atom of the reactant hydrocarbon compound in place of the hydrogen atom thereby producing an oxidized hydrocarbon compound in an amount which is less than or equal to a corresponding stoichiometric amount of the reactant metal ion reducing agent, the acid counter ion bonded to the one carbon atom of the oxidized hydrocarbon compound rendering such carbon atom less reactive towards oxidation than such carbon atom is in the reactant hydrocarbon compound.

15. The method of oxidizing a hydrocarbon compound of claim 14 further comprising recycling the higher valence state metal ion to a lower valence state for oxidizing more of the hydrocarbon compound.

16. The method of oxidizing a hydrocarbon compound of claim 14 wherein the acid solution comprises a fully fluorine substituted carboxylic acid.

17. The method of oxidizing a hydrocarbon compound of claim 14 wherein the hydrocarbon compound is selected from the group consisting of propane, methane and cyclohexane.

18. The method of oxidizing a hydrocarbon compound of claim 14 wherein the metal ion reducing agent comprises Cu(I).

19. The method of oxidizing a hydrocarbon compound of claim 14 wherein the compound containing two oxygen atoms is $O_2$.

20. The method of oxidizing a hydrocarbon compound of claim 14 wherein, the acid solution comprises a fully fluorine substituted carboxylic acid; and the metal ion reducing agent comprises Cu(I).

21. The method of oxidizing a hydrocarbon compound of claim 14 wherein, the acid solution comprises a fully fluorine substituted carboxylic acid;

the hydrocarbon compound is selected from the group consisting of propane, methane and cyclohexane; and the metal ion reducing agent comprises Cu(I).

22. The method of oxidizing a hydrocarbon compound of claim 14 wherein the effective temperature is from 20° C. to 49° C.

23. The method of oxidizing a hydrocarbon compound of claim 14 wherein the effective pressure is from atmospheric to 500 psig.

24. The method of oxidizing a hydrocarbon compound of claim 14 wherein the sufficient amount of time is from 5 minutes to 12 hours.

25. The method of oxidizing a hydrocarbon compound of claim 14 wherein the effective temperature is from 20° C. to 49° C. and the effective pressure is from atmospheric to 500 psig.

26. The method of oxidizing a hydrocarbon compound of claim 14 wherein the effective temperature is from 20° C. to 49° C., the effective pressure is from atmospheric to 500 psig, and the sufficient amount of time is from 5 minutes to 12 hours.

27. The method of oxidizing a hydrocarbon compound of claim 14 wherein, the hydrocarbon compound is selected from the group consisting of propane, methane and cyclohexane;

the effective temperature is from 20° C. to 49° C.; and the effective pressure is from atmospheric to 500 psig.

28. The method of oxidizing a hydrocarbon compound of claim 14 wherein the hydrocarbon is an alkane.

29. The method of oxidizing a hydrocarbon compound of claim 14, wherein the hydrocarbon compound is a linear alkane.

30. The method of oxidizing a hydrocarbon compound of claim 14 wherein the hydrocarbon compound is a cyclic hydrocarbon.

31. The method of oxidizing a hydrocarbon compound of claim 14 wherein the hydrocarbon compound is non-aromatic.

32. The method of oxidizing a hydrocarbon compound of claim 14 wherein the metal ion reducing agent comprises Fe(II).

33. A method of oxidizing a reactant hydrocarbon compound in a single vessel comprising:

combining in a single vessel trifluoroacetic acid, a reactant hydrocarbon compound which is soluble in trifluoroacetic acid, a compound containing two oxygen atoms bonded to one another, and a reactant metal ion reducing agent capable of reducing one of the oxygen atoms of the compound containing two oxygen atoms bonded to one another, and thereby forming a mixture, the hydrocarbon compound having at least one carbon atom bonded to a hydrogen atom; and maintaining the mixture at an effective temperature and effective pressure for a sufficient amount of time to, a) reduce one of the oxygen atoms in the compound containing two bonded oxygen atoms with the metal ion reducing agent, b) oxidize the reactant metal ion reducing agent to a higher valence state, and c) bond trifluoroacetate counter ion of the trifluoroacetic acid to the one carbon atom of the hydrocarbon compound in place of the hydrogen atom thereby oxidizing the hydrocarbon compound into an amount of a trifluoroacetate, the amount of trifluoroacetate being less than or equal to a corresponding stoichiometric amount of the reactant metal ion reducing agent.

34. The method of oxidizing a hydrocarbon compound of claim 33 further comprising recycling the higher valence state metal ion to a lower valence state for oxidizing more of the hydrocarbon compound.

35. The method of oxidizing a hydrocarbon compound of claim 33 wherein the hydrocarbon compound is selected from the group consisting of propane, methane and cyclohexane.

36. The method of oxidizing a hydrocarbon compound of claim 33 wherein the metal ion reducing agent comprises Cu(I).

37. The method of oxidizing a hydrocarbon compound of claim 33 wherein the compound containing two oxygen atoms is $O_2$.

38. The method of oxidizing a hydrocarbon compound of claim 33 wherein the hydrocarbon compound is an alkane.

39. The method of oxidizing a hydrocarbon compound of claim 33 wherein the hydrocarbon compound is a linear alkane.

40. The method of oxidizing a hydrocarbon compound of claim 33 wherein the hydrocarbon compound is a cyclic hydrocarbon.

41. The method of oxidizing a hydrocarbon compound of claim 33 wherein the hydrocarbon compound is non-aromatic.

42. The method of oxidizing a hydrocarbon compound of claim 33 wherein the metal ion reducing agent comprises Fe(II).

43. A method of oxidizing a hydrocarbon compound in a single vessel in an acid solution, the acid solution comprising $H^+$ ion and a counter ion, the method comprising the following steps:

reacting Cu(I) with $O_2$ and $H^+$ in the acid solution to oxidize the Cu(I) to Cu(II) and form hydroperoxyl radical;

reacting hydroperoxyl radical with Cu(I) and $H^+$ in the acid solution to oxidize Cu(I) to Cu(II) and form $H_2O_2$;

reacting $H_2O_2$ with Cu(I) in the acid solution to form $OH^-$, Cu(II) and hydroxyl radical;

reacting hydroxyl radical with a hydrocarbon compound in the acid solution to form $H_2O$ and an organic radical; and reacting the organic radical with Cu(II) and the acid counter ion to combine the counter ion and organic radical into an ester compound.

44. The method of oxidizing a hydrocarbon compound of claim 43 wherein the acid solution comprises a fully fluorine substituted carboxylic acid.

45. The method of oxidizing a hydrocarbon compound of claim 43 wherein reacting conditions within the single vessel are from about 20° C. to 70° C. and from about atmospheric pressure to 500 psig.

46. The method of oxidizing a hydrocarbon compound of claim 43 wherein Cu(I) is converted to Cu(II) in the method, and the method further comprising recycling Cu(II) to a lower valence state for oxidizing more of the hydrocarbon compound.

47. The method of oxidizing a hydrocarbon compound of claim 43 wherein the hydrocarbon compound is methane.

48. The method of oxidizing a hydrocarbon compound of claim 47 wherein the acid solution comprises a fully fluorine substituted carboxylic acid.

49. The method of oxidizing a hydrocarbon compound of claim 43 wherein the hydrocarbon compound is an alkane.

50. The method of oxidizing a hydrocarbon compound of claim 43 wherein the hydrocarbon compound is a linear alkane.

51. The method of oxidizing a hydrocarbon compound of claim 43 wherein the hydrocarbon compound is a cyclic hydrocarbon.

52. The method of oxidizing a hydrocarbon compound of claim 43 wherein the hydrocarbon compound is non-aromatic.

53. A method of oxidizing a reactant hydrocarbon compound in a single vessel comprising:

combining in a single vessel the reactant hydrocarbon compound, an acid solution in which the reactant hydrocarbon compound is soluble, a compound containing two oxygen atoms bonded to one another, a metal ion reducing agent selected from the group consisting of Cu(I), Fe(II), and mixtures thereof, and thereby forming a mixture; the acid solution comprising $H^+$ ion and an acid counter ion, the reactant hydrocarbon compound having at least one carbon atom bonded to a hydrogen atom; and maintaining the mixture at an effective temperature and effective pressure for a sufficient amount of time to in the acid solution, a) reduce one of the oxygen atoms in the compound containing two bonded oxygen atoms with the metal ion reducing agent and thereby oxidize the metal ion reducing agent, and b) bond the acid counter ion to the one carbon atom of the reactant hydrocarbon compound in place of the hydrogen atom thereby producing an oxidized hydrocarbon compound, the acid counter ion bonded to the one carbon atom of the oxidized hydrocarbon compound rendering such carbon atom less reactive towards oxidation than such carbon atom is in the reactant hydrocarbon compound.

54. The method of oxidizing a hydrocarbon compound of claim 53 wherein the acid solution comprises a fully fluorine substituted carboxylic acid.

55. The method of oxidizing a hydrocarbon compound of claim 53 wherein the hydrocarbon compound is selected from the group consisting of propane, methane and cyclohexane.

56. The method of oxidizing a hydrocarbon compound of claim 53 wherein the compound containing two oxygen atoms is $O_2$.

57. The method of oxidizing a hydrocarbon compound of claim 53 wherein the reactant metal ion reducing agent comprises Cu(I), the Cu(I) being provided by a reaction in the single vessel of Cu(0) and Cu(II) to produce Cu(I), the step of oxidizing the metal ion reducing agent oxidizing the Cu(I) to Cu(II).

58. The method of oxidizing a hydrocarbon compound of claim 53 wherein the hydrocarbon compound is an alkane.

59. The method of oxidizing a hydrocarbon compound of claim 53 wherein the hydrocarbon compound is a linear alkane.

60. The method of oxidizing a hydrocarbon compound of claim 53 wherein the hydrocarbon compound is a cyclic hydrocarbon.

61. The method of oxidizing a hydrocarbon compound of claim 53 wherein the hydrocarbon compound is non-aromatic.

62. A method of oxidizing a hydrocarbon compound in a single vessel in an acid solution, the acid solution comprising $H^+$ ion and a counter ion, the method comprising the following steps:

reacting Cu(I) with $O_2$ and $H^+$ in the acid solution to oxidize the Cu(I) to Cu(II) and form hydroperoxyl radical;

reacting hydroperoxyl radical with Cu(I) and $H^+$ in the acid solution to oxidize Cu(I) to Cu(II) and form $H_2O_2$;

reacting $H_2O_2$ with Cu(I) in the acid solution to form $OH^-$, Cu(II) and hydroxyl radical;

reacting hydroxyl radical with Cu(II) to form a Cu(III) oxidizing intermediate; and reacting the Cu(III) oxidizing intermediate with a hydrocarbon compound in the acid solution to oxidize the hydrocarbon compound into an ester compound.

63. The method of oxidizing a hydrocarbon compound of claim 62 wherein the hydrocarbon compound is an alkane.

64. The method of oxidizing a hydrocarbon compound of claim 62 wherein the hydrocarbon compound is a linear alkane.

65. The method of oxidizing a hydrocarbon compound of claim 62 wherein the hydrocarbon compound is a cyclic hydrocarbon.

66. The method of oxidizing a hydrocarbon compound of claim 62 wherein the hydrocarbon compound is non-aromatic.

* * * * *